United States Patent [19]

Updike

[11] 4,138,474
[45] Feb. 6, 1979

[54] METHOD AND DEVICE FOR IMMUNOASSAY

[75] Inventor: Stuart J. Updike, Madison, Wis.

[73] Assignee: Wisconsin Alumni Research Foundation, Madison, Wis.

[21] Appl. No.: 356,092

[22] Filed: May 1, 1973

[51] Int. Cl.² .................. G01N 33/16; A61K 43/00
[52] U.S. Cl. ................................. 424/1; 23/230 B; 23/230.6; 424/12; 210/31 C; 210/504; 422/58; 422/101
[58] Field of Search ............... 23/230 B, 259; 424/1, 424/12; 252/316; 210/31 C, 504

[56] References Cited

U.S. PATENT DOCUMENTS

| | | | |
|---|---|---|---|
| 3,105,012 | 9/1963 | Brandon et al. | 424/12 |
| 3,215,500 | 11/1965 | Bittner | 23/259 |
| 3,451,777 | 6/1969 | DiGiulio | 23/230 B |
| 3,616,936 | 11/1971 | Johansson et al. | 210/504 |
| 3,711,247 | 1/1973 | Adams | 23/230 B |
| 3,793,445 | 2/1974 | Updike et al. | 424/12 |
| 3,794,467 | 2/1974 | Adams et al. | 23/230 B X |
| 3,802,843 | 4/1974 | Kim | 23/230 B X |

OTHER PUBLICATIONS

Bernfeld, *Science*, v. 142, pp. 678–679, (1963).
Hicks et al., *Analytical Chemistry*, v. 38, pp. 726–730, (1966).
*Chem. Abstr.*, v. 73: 127610m (1970).
*Chem. Abstr.*, v. 74: 123000k (1971).
*Chem. Abstr.*, v. 75: 33018p (1971).

*Primary Examiner*—Sidney Marantz
*Attorney, Agent, or Firm*—McDougall, Hersh & Scott

[57] ABSTRACT

A method and device for immunological determinations wherein the device comprises a container housing a volume of dry, insoluble, yet highly hydrophilic, gel particles, containing binding protein or combinations of binding protein and radio-active tag material and in which the dry gel particles are characterized by pores of a size that permit entry of low molecular weight components into the intra gel volume but insufficient to permit entry of large molecular weight components which remain in the extra gel volume.

4 Claims, 1 Drawing Figure

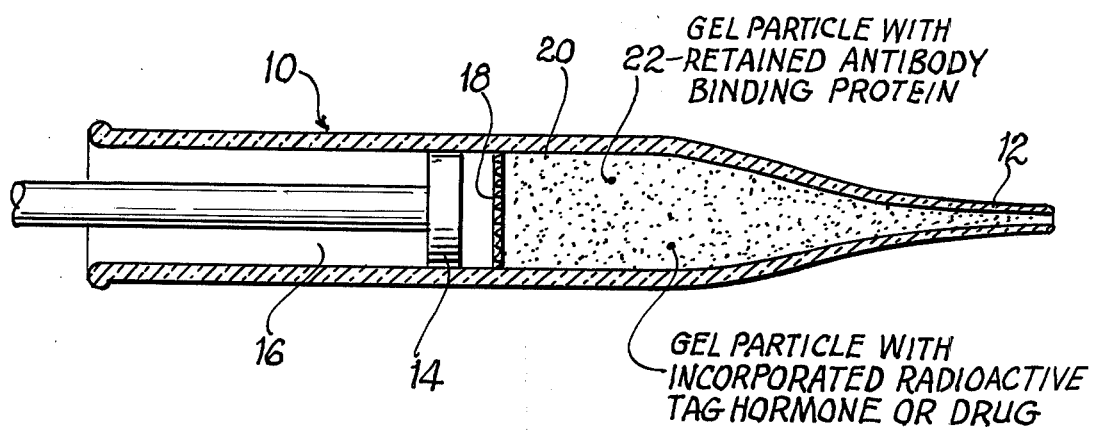

METHOD AND DEVICE FOR IMMUNOASSAY

This invention relates to clinical techniques for immunological determinations and to elements employed in making such determinations and it relates more particularly to a new and improved device for radioimmunoassay (RIA).

Techniques that have been reported for radioimmunoassay to determine polypeptide hormones of immediate clinical interest have been arduous and/or too unreliable for widespread adoption in the clinical laboratory.

It has been found that concepts which are described in the copending application Ser. No. 33,098, filed Apr. 29, 1970, and entitled "Reagent for Immunological Determinations" now U.S. Pat. No. 3,793,445 issued Feb. 19, 1974 can be adapted to a simple, low cost, stable device capable of utilization in an easy and efficient manner to give reliable determinations and which therefore enables immunological determinations or such radioimmunoassays to find wider acceptance in the clinical laboratory.

This invention also has as an object a method and means by which interfering components of high molecular weight can be separated from components of low molecular weight, as in blood or blood plasma, to enable utilization or determinations to be made of one component separate and apart from the other or without interference by the other. This later concept which came to light during the development of the device for the immunological determinations has a number of practical applications other than in radioimmunoassays, as will hereinafter be described.

In the aforementioned copending application, description is made of a gel matrix of an insoluble, wettable hydrophilic polymer in which at least one protein, having one or more binding sites, is entrapped therein, with the gel matrix having a pore size small enough to prevent diffusion of the binding protein from the gel but sufficient to permit a low molecular weight antigen to diffuse into the gel matrix to reach the binding site.

Proteins having a binding capacity for certain specific smaller molecules and which can be readily immobilized in the polymer gel are illustrated by various protein globulins and antibodies.

Gel systems having such globulins or antibodies entrapped therein can be used effectively for analyzing for a variety of antigens or haptens, such as drugs, polypeptide hormones and steroid hormones. Antigens and haptens susceptible of being assayed in a system of the type described include, for example, angiotensin, insulin, growth hormone, gonadotropic hormone, parathyroid hormone, glucagon, cortisol, prostoglandin, corticosteroids, cyclic fatty acid hormones and estrogen, and drugs such as digoxin, thyroxin, morphine, digitalis, and the like. By way of example, specific corticosteroid binding globulins, immobilized by entrapment in the gel system, permit assay of corticosteroid hormones in addition to the many polypeptide hormones. Specifically, 7S gamma-globulin (150,000 m.w.) can be used to assay for angiotensin (1,000 m.w.).

In accordance with the practice of this invention, the gel matrix, with the entrapped binding protein, is embodied in a simple unit assembly which permits sample assay without influence by high molecular weight interferences such as proteolytic enzymes, and whereby reliable determinations can be made in a simple, easy and efficient manner. The invention will be described in greater detail by reference to the following examples, but it will be understood that the concepts described have application to other assays, with units of different shape or construction, but in which the gel matrix with the entrapped binding protein is still employed in a dry form, such as freeze-dried, alcohol-dried and the like, hereinafter referred to as the lyophilized form.

EXAMPLE 1

A gel, in which dilute anti-angiotensin immune serum containing 7S gamma-globulin (m.w. 150,000) is entrapped in a gel matrix having a pore size to enable diffusion of angiotensin (m.w. 1,050) for assay is prepared as follows:

8 Grams of acrylamide and one gram of N,N'-methylenebis-acrylamide is dissolved to a final volume of 36 ml in sodium phosphate buffer solution (0.1 M, pH 7.4) containing a suitable dilution of antiserum. To the resulting solution 0.1 ml of a suspension of 100 mg of riboflavin in 20 ml of distilled water and 0.02 ml of N,N,N',N'-tetramethyl-ethylenediamine is added, followed by 0.2 mg of sodium hydrosulfite. The admixture, in a suitable vessel, is stoppered and agitated and then is exposed to light from an ordinary tungsten electric light bulb to induce photopolymerization. The polymerization is complete in 5–15 minutes. The reaction vessel is continuously chilled in an ice water bath as needed to prevent the heat generated by the exothermic polymerization reaction from adversely affecting the binding protein.

EXAMPLE 2

The gel system of Example 1 is reduced to fine particles, preferably within the range of −40 to +80 mesh. The particles are then washed with water or dilute buffer solution and then dried by lyophilization or dried by water extraction using an organic solvent such as 95% ethanol followed by evaporation of the organic solvent.

RIA depends on being able to precisely control the number of binding sites in the test system. This is achieved by dispensing the dry gel particles volumetrically.

The binding proteins, immobilized in the dry gel particles are stable in that they become relatively insensitive to time and temperature. As a result, they maintain their potency over extended periods of time until used.

EXAMPLE 3

Evaluation device:

In its simplest form, an evaluation device for radioimmunoassay is illustrated in the attached figure in the form of a syringe 10, such as a 1 ml tuberculin syringe, having a syringe needle 12 at one end and a plunger 14 operative in an elongate barrel at the other end for drawing fluid through the needle 12 into the body portion 16 of the syringe in response to the generation of volumne conditions upon withdrawal of the plunger.

Adjacent the needle end portion, the syringe is subdivided by a porous barrier 18 into a calibrated portion 20 packed with a column of prescribed volume of the dry gel particles of Examples 1 and 2, while the plunger or other withdrawal means communicates with the portion beyond the barrier 18.

In the illustrated modification, the barrier is in the form of a nylon fabric or net having openings too small to permit passage of the gel particles. In the illustrated modification 33 mg of dry gel particles are packed in the volume of 0.14 ml enclosed by the porous barrier made up of about two-thirds intra gel volume and about one-third extra gel volume (or voids) with the dry gel particles having a water regain of 100 mg water per 33 mg gel particles.

The device can be packed into immunoassay kits with one or more other devices packed with dry gel particles in which other binding proteins are entrapped for assay of other antigens or haptenes.

EXAMPLE 4

Method of use:

In use, the needle 12 is inserted into the sample (serum, plasma or whole blood directly from a vein) and the plunger 14 is pulled back to draw some of the liquid sample into the syringe 10 in an amount to fill the volume 20 below the barrier 18 and preferably in an amount to at least cover the net.

As the sample is drawn into the syringe, the highly hydrophilic gel particles 22, by rehydration, absorb a predictable and reproducible portion of low molecular components in the sample. To prevent coagulation, when testing fresh whole blood, or plasma, it is desirable to incorporate an anticoagulant in the gel recipe from which the dry gel particles are formed.

The size of the sample that is taken up by the particles depends upon the water regain value of the gel as well as the amount of particles present in the column, measured by weight or volume. As a result, sample size can be automatically controlled by the amount and water regain value of the dried gel particles thereby to make the test reproducible and accurate, independent of the amount of liquid sample that is drawn into the syringe.

After the sample has been drawn into the syringe, thus wetting the dry gel particles, the void volume (extra gel volume of the miniature-syringe chromatographic column) is flushed out, as with a buffer solution such as 0.1 M phosphate buffer or any other physiological solution and the like. The flushing liquid should be employed in an amount of at least one void or extra gel volume but it is desirable to make use of more than one void volume, such as from two to five void volumes to insure the removal of sample component remaining in the extra gel volume. The low molecular weight polypeptide hormone (or other antigen or haptene) remains substantially entrapped within the intra gel space during this rapid column wash step for removing high molecular weight interferences. Thus high molecular weight interferences can be removed with the wash solution used to flush the column of gel particles.

After the flushing step, a competing radioactive "tag" hormone of known concentration is drawn into the syringe in an amount to at least fill the void volume and preferably in an amount greater than one void volume.

The unit is then incubated for a specified period of time, which may range from 30 seconds to 30 hours at room temperature. It is not necessary for the radio competitive binding assay to go completely to equilibrium before final separation of bound from free radioactivity.

Thereafter, a buffered wash solution, which may be the same as that used to flush the column in the previous step, is passed through the column. This operates to separate unbound hormones from the bound hormones. The column is flushed with sufficient volume for a sufficient length of time to substantially complete the separation step.

The total amount of tagged radioactive hormone used will equal the bound plus the unbound. The radioactivity bound to the binding sites in the column can be measured directly or it can be determined indrectly by measuring the radio activity of the wash solution. Use can be made of standard values sufficient to construct a standard working curve having the per cent bound as the abscissa and the log scale of standard as the base, whereby the unknown in the sample can be directly read from the curve, in accordance with the standard procedures employed in current radioimmunoassay.

Returning now to the specific elements of the test unit, various modifications and ramifications are possible.

The formulation of the gel of which the particles are formed is not significant since use can be made of any gel forming material which is capable of being reduced into porous, insoluble, highly hydrophilic particles of controlled pore size. Thus, other highly hydrophilic, insoluble gels capable of the desired pore size and drying or lyophilization can be used, but it is preferred to make use of polyacrylamide gels of the type described in the aforementioned application, wherein an acrylamide monomer and cross linking reagent are combined with sufficient cross linking agent to stabilize the pore size and support the monomer not only to provide the desired pore size but to give the gel the density desired for rapid sedimentation in particulate form and to provide sufficient rigidity to the gel particles. As described in the aforementioned application, the ratio of one part by weight cross linking agent to 4 to 10 parts by weight monomer is sufficient to give a gel having a total polymer gel concentration in the range of 12–35%.

The binding globulin, antibody, or protein embodied within the dry gel particles can be varied, depending upon the hormone, drug or other material to be assayed, such as angiotensin, insulin, growth hormone, gonadotropic hormone, parathyroid hormone, cortisol, digoxin, digitalis or thyroxin.

By way of further modification, the radioactive tag hormone can also be incorporated in calibrated amounts within gel particles. These gel particles which, upon rehydration, release radioactively tagged hormone, can also be added in precise amount by weight or volume to the dry antibody gel particles, used as the binding reagent in the RIA system so that the addition of radioactively tagged hormone into the RIA system is automatic. In this arrangement, it is desirable to make use of an amount of tagged hormone or drug which will not completely satisfy the binding sites available in the gel particles before the unknown sample is drawn into the column.

In a similar fashion, a standard amount of drug or hormone can be incorporated into the gel recipe for release upon rehydration of the gel particles in the test system. Thus, for calibration purposes, the user can be provided with the convenience of pre-addition of standard to the RIA system which is automatically released upon rehydration of the gel particles.

EXAMPLE 5

The foregoing modification contemplates the formation of dry gel particles containing the tag hormone in a manner similar to that for producing the dry gel particles containing the binding protein, but separate and apart therefrom. The gel particles containing the tag hormone and the gel particles containing the antibody or binding protein would then be mixed in the amounts described and the mixture would then be employed to form the volume in the test unit. Upon rehydration, the tag hormone would become free to reach the antibody binding sites.

It has also been found possible to combine the antibody binding protein and the tag hormone in the same gel particles, without premature binding of the tag hormone to antibody binding sites, thereby to eliminate the need for separate preparation of the gel particles and to form a premix thereof.

For this purpose, it is important to effect the incorporation of the tag hormone in the absence of hydration which would enable the tag hormone to reach the binding sites. This can be accomplished by the addition of the tag hormone to the dry gel particles from a non-aqueous medium. Thus incorporation of the tag hormone is carried out when the antibody-gel particles are dry—which should preclude premature binding of the tag hormone to antibody binding sites.

EXAMPLE 6

Dry gel particles with immobilized antibody activity, prepared in accordance with Examples 1 and 2, are contacted with a solution of the tagged hormone in 95% ethanol or other organic alcohol or solvent.

The particles are dried as in air or in a chromatographic column having clean air flowing therethrough to effect alcohol removal.

The resulting dry gel particles have both antibody binding protein activity and tagged hormone in a non-complex (non-bound) form. The tagged hormone will not diffuse to the binding site until the gel undergoes rehydration with the test sample, as in EXAMPLE 4. At such time, the tagged hormone is released to compete with the sample hormone for complexing to the binding sites.

The water regain value of the gel particles determines how much sample reaches the antibody binding protein contained in the intra gel compartment. The water regain of the gel will depend somewhat on the percent polymer and percent cross linking reagent and more particularly on the thoroughness of the drying process. The gel reagents of the types described can be dried so that the water regain will not change under the conditions of temperature and humidity used in storage, and this is the preferred degree of dryness. Other degrees of dryness and water regain can be used, but are not as convenient, because of changes of hydration that occur with changes of storage temperature and humidity. The particle size as well as the form and shape of the dry gel particles can be varied depending upon the size and shape of the test device.

Instead of a syringe, other containers can be employed in which known volume or weight of dry gel particles can be retained and through which the liquid sample, flush solution and tag solution can be pulled or pushed for engagement with the gel particles in the amounts previously described. In the event that a device is used in which the gel particles are retained as a column in an intermediate section of known volume, barriers, such as the nylon net or other porous layers, should be provided at opposite ends to confine the particles into the column while enabling the various fluids to pass therethrough into and out of the column of particles.

This porous barrier is employed for the automatic separation of bound from unbound radioactivity, which occurs during the flushing of the column. This porous structure also acts as an anticonvection barrier, which discourages mixing of any solution sequestered outside the gel particle compartment, but which still is confluent with the gel particle compartment during the incubation step of RIA.

Since the volume of gel particles is known and the water regain is constant, the amount of sample taken up by the dry gel particles will be the same independent of the size of the sample or the amount taken up into the test unit. The same applies with respect to the fluid solution used to flush the particles for removal of material in the extra gel volume and the amount of radioactive tag material to which the gel particles are ultimately exposed. Thus, many of the steps which are critical to prior radioimmunoassays can be eliminated with equal or greater reproducibility and accuracy of test results. Since the antibody is insolubilized and immobilized in the gel particles, the conventional centrifugation and wash steps, employed in current procedures, can be eliminated in their entirety in preparation and use of the test unit of this invention.

Similarly, since the unknown and tag material taken up depends on such known values as volume and water regain, the critical steps of pipetting or aliquoting and the numerous errors associated therewith are eliminated thereby to increase the accuracy of the analysis.

By immobilizing the antibody binding reagent in a gel, the centrifugation step of RIA can be eliminated, and by drying the gel particles, sample application without pipetting is achieved, as discussed above. Furthermore, by encaging the antibody binding protein molecule in a gel polymer matrix, high molecular weight (HMW) interferences of RIA can be excluded. These HMW interferences are to be found in some, but not all biological samples, and are of two types: (1) proteolytic enzymes, which can degrade polypeptide hormone, and (2) endogenous antibody, which can bind polypeptide hormone. For example, carboxypeptidase, a proteolytic enzyme, can degrade the polypeptide hormone, angiotensin. Endogenous antibody that binds insulin is frequently found in patients treated with injections of bovine or porcine insulin. These high molecular weight interferences are too large to penetrate into the polymer matrix of the gel particle, and so are sequestered in the extra gel space, where they can be removed by a rapid wash of the gel column.

Concepts employed in the practice of the described invention have important utilization other than in radioimmunoassays. Under such circumstances, utilization can be made of the dry gel particles without entrapped binding protein.

Thus, an important further concept of this invention resides in the utilization of dry gel particles of a predetermined pore size and water regain value whereby use can be made thereof to remove a calibrated increment of sample for testing independent of the size of the sample. The dry gel particles take up only so much sample no matter how much reagent is passed through. For example, dry gel particles having a predetermined water regain value, in equal amounts measured by volume or weight, will reproducibly take up precise amounts of liquid containing molecules below a maximum size for subsequent test, independent of the size of the sample and without the need for the conventional less accurate practice of pipetting a measured amount of the sample.

Water regain value of the dry gel particles remains sufficiently constant to enable the removal of aliquot sample protions of equal amount merely by use of the more accurate and rapid techniques of measurement, as by weight or by volume, of the lyophilized gel particles to which the liquid samples are exposed.

A still further important concept of this invention resides in the utilization of the dry gel particles per se, with controlled pore size, as a means and method to effect separation of high molecular weight interfering components or molecules from low molecular weight components or molecules, mereby by contacting the liquid sample with the dry gel particles having high water regain value and a pore size sufficient to permit entry of low molecular weight components or molecules but insufficient to permit entry of high molecular weight components or molecules. Thereafter the gel particles can be flushed with a reagent to wash out the high molecular weight components from the extra gel volume or void, leaving an aliquot portion of the low molecular weight components or molecules entrapped within the intra gel volume for testing or use. Instead, the entrapped low molecular weight components or molecules can be eluted or otherwise recovered from within the intra gel volume for testing or use separate and apart from the gel particles.

Such fractionation technique using dry gel particles of the desired small pore size and high water regain, finds particular value in separation of high molecular weight interfering compounds from low molecular weight compounds in blood plasma, whole blood, serum and the like. For such purpose, the blood or plasma is contacted with the dry gel particles having a high water regain value and a pore size sufficient to permit entry only of the low molecular weight components but insufficient to permit entry of the high molecular weight interfering components. The latter remain in the extra gel volume from which they can be flushed for separation from the low molecular weight components entrapped within the gel particles.

Because the gel particles are dry and hydrophilic, the water regain can be employed as a means to measure out a sample without pipetting. The intra gel compartment has a water regain that is reproducible from column to column, whether overfilled or underfilled and the amount of sample removed will be exactly the same. Because of the entry of components below a particular molecular weight, while holding out higher molecular weight components incapable of entry through the pores, a measured increment of sample, purified from the standpoint of a particular molecular weight fraction, can be removed for testing without the presence of interfering molecules and without the need for centrifuge, pipetting or the like. The low molecular weight component can be tested in situ or eluted from the gel particles for use or testing. Thus one can achieve the important combination of elution and measurement of sample volume simultaneously with separation.

Chemical assays in the clinical laboratory generally require the addition of a precise amount of sample to the assay system. Analysis of whole blood sample frequently requires separation of serum or plasma from red blood cells and deproteinization before the serum or plasma sample is added to the assay system. This type of sample preparation classically has required centrifugation. However, the invention described herein allows an automatic selection and separation of a precise low molecular weight fraction away from both cellular and protein elements of blood. A variety of low molecular weight anticoagulants, for example, EDTA, citrate, and heparin, can be incorporated in the dry gel particles and activated upon contact with whole blood. In this way, clotting of the assay sample is prevented.

Thus it will be apparent that the concepts described find application clinically in chemistry laboratories as well as in radioimmunoassays.

It will be understood that changes may be made in the details of construction, arrangement and operation without departing from the spirit of the invention, especially as defined in the following claims.

I claim:

1. A method for radioimmunoassay with a device comprising a container housing a volume of dry, highly hydrophilic, insoluble gel particles containing a binding protein and a competing radioactive tag material, and characterized by pores of a size which will prevent binding protein from diffusing from the gel and permit diffusion of small molecules into the intra gel volume, and means for transmission of fluid for determination into and out of said volume, comprising the steps of exposing the dry gel particles to a fluid system to be determined to wet the gel particles whereby molecular weight components in the fluid system small enough to penetrate the pores enter into the intra gel volume while components of a larger molecular weight remain in the extra gel volume, the tag material pre-incorporated into the system being automatically released when the sample fluid hydrates the gel particles, incubating the system and then washing the gel particles with at least one void volume of a wash solution to separate the unbound tag material from the bound tag material, and then measuring the radioactivity of the bound or unbound tag material.

2. A device for immunological determinations of a fluid system comprising an enclosure, a hollow needle communicating with one end of the enclosure, a porous barrier spanning the enclosure in spaced relation with the needle end to define a volume therebetween, dry highly hydrophilic, insoluble gel particles, a binding protein and a competing radioactive tag material within said gel particles, in which said gel particles are characterized by pores of a size which will prevent said binding protein from diffusing from the gel while permitting diffusion of small molecules into the intra gel volume, said gel particles filling the said volume within the enclosure, and means in communication with the enclosure beyond the porous barrier for drawing fluid to be tested through the needle and into and through the said volume.

3. A device as claimed in claim 2 in which the tag material and the binding protein are in separate dry gel particles.

4. A device as claimed in claim 2 in which the tag material and the binding protein are in the same dry gel particles.

* * * * *

UNITED STATES PATENT OFFICE
CERTIFICATE OF CORRECTION

Patent No. 4,138,474  Dated February 6, 1979

Inventor(s) Stuart J. Updike

It is certified that error appears in the above-identified patent and that said Letters Patent are hereby corrected as shown below:

In the specification, page 1, before the first paragraph insert the following paragraph:

-- The invention described herein was made in the course of work under a grant or award from the Department of Health, Education, and Welfare. --

Signed and Sealed this

Twelfth Day of June 1979

[SEAL]

Attest:

RUTH C. MASON
Attesting Officer

DONALD W. BANNER
Commissioner of Patents and Trademarks